United States Patent [19]

Brejnik et al.

[11] 4,101,071
[45] Jul. 18, 1978

[54] ELECTRONIC CALORIE COUNTER

[76] Inventors: Carl Brejnik, 1327 S. 79th, Omaha, Nebr. 68124; William T. Whitlow, 217 W. Park La., Waterloo, Iowa 50701

[21] Appl. No.: 783,974

[22] Filed: Apr. 4, 1977

[51] Int. Cl.$^2$ ............................................. G06M 3/06
[52] U.S. Cl. ......................... 235/92 MT; 128/2.05 T; 235/92 TF; 235/92 DP; 235/92 R; 364/415
[58] Field of Search .......... 235/92 T, 92 GA, 92 MT, 235/92 CP, 92 DP, 92 TF, 92 FQ, 156; 58/152 R, 23 R; 128/2.05 T, 2.06 F; 272/DIG. 3, DIG. 5, DIG. 6, 73, 132

[56] References Cited

U.S. PATENT DOCUMENTS

| 3,717,140 | 2/1973 | Greenwood | 128/2.06 F |
| 3,863,626 | 2/1975 | Huber | 128/2.06 F |
| 3,978,849 | 9/1976 | Geneen | 128/2.06 F |
| 3,984,666 | 10/1976 | Barron | 235/92 MT |

FOREIGN PATENT DOCUMENTS

| 1,312,107 | 4/1973 | United Kingdom | 128/2.06 F |

Primary Examiner—Joseph M. Thesz
Attorney, Agent, or Firm—Zarley, McKee, Thomte, Voorhees & Sease

[57] ABSTRACT

A calorie counter which is adapted to be constructed in the shape of a wristwatch and which includes a pulse detector mounted in the band of the watch to detect the heart pulses. The calorie counter circuit is comprised of six sections; the time base, clock, data accumulator, translator, data selector, and the display. The heart pulses are detected by the pulse detector and are supplied to the calorie counter circuit which has been preprogrammed for each pulse rate from 40 pulses/minute to 199 pulses/minute. The calorie count for each minute of time represents a total of calorie count for a predetermined length of time. The accumulated information is converted by the driver circuit which converts and processes the binary coded decimal information into drive lines for the display numbers in the display section. A manual control is used to select the desired format of display; i.e., time, calorie/minute, or calories total.

7 Claims, 7 Drawing Figures

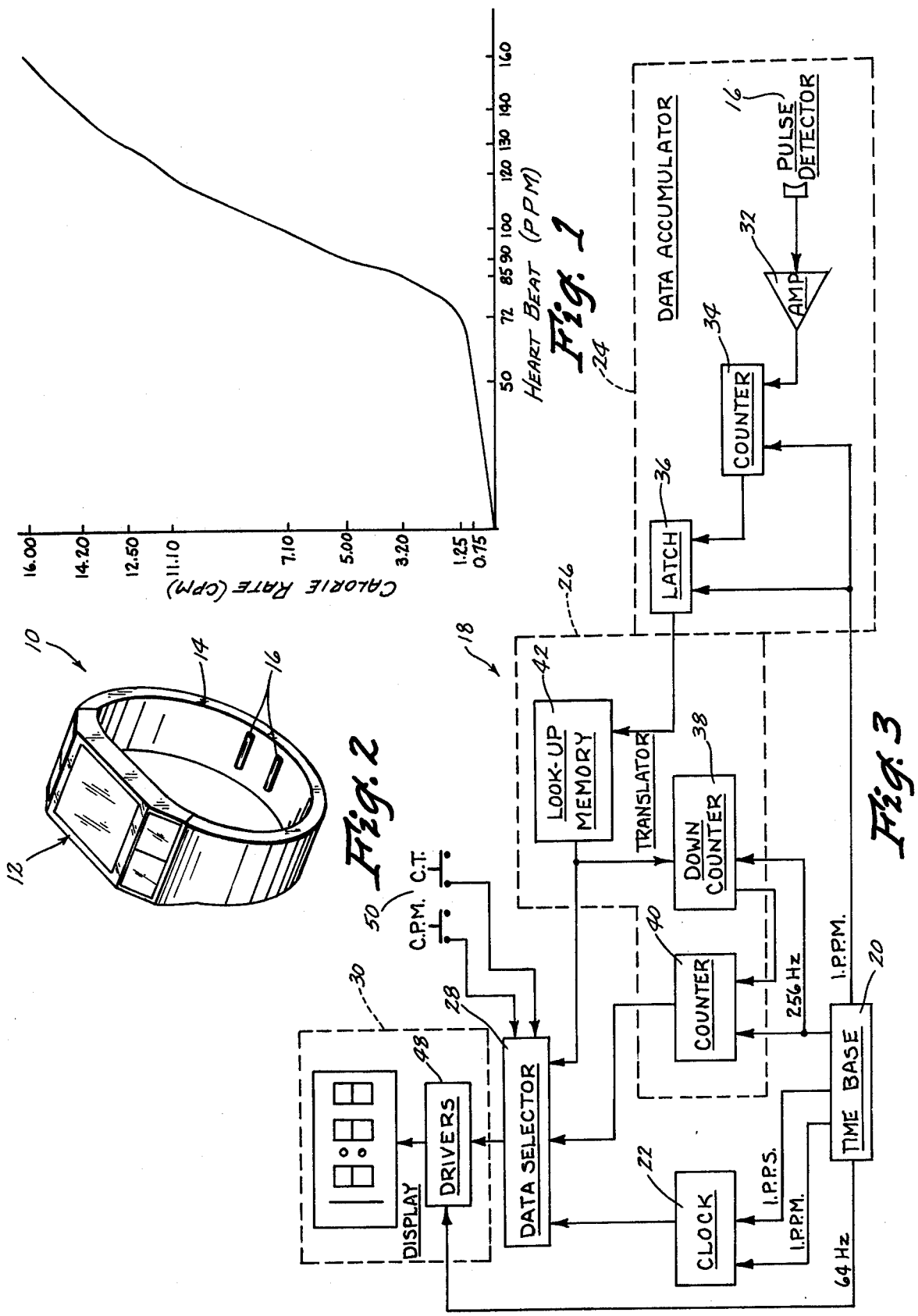

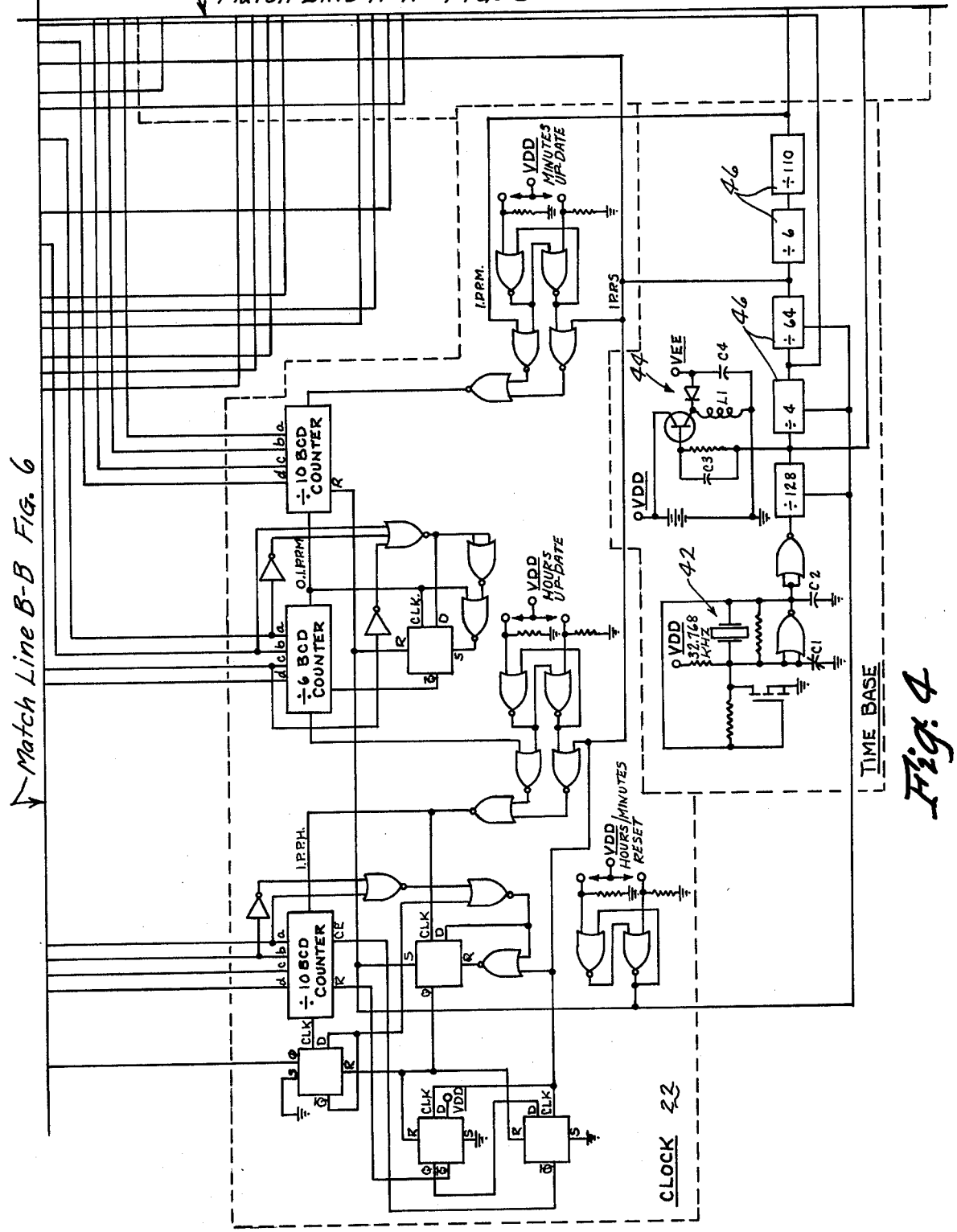

ELECTRONIC CALORIE COUNTER

BACKGROUND OF THE INVENTION

Recent studies support the theory that the pulse rate of the individual at any given time is related to the number of calories burned by the person. FIG. 1 illustrates a chart which compares the calorie burn rate versus the pulse rate. As seen in FIG. 1, the calorie burn rate is not directly proportional to the pulse rate but varies somewhat. Thus, if a person has a pulse rate of 140 pulses per minute, he will be burning approximately 16 calories per minute.

Thus it can be seen that a person will burn more calories if his heart is beating faster than if he had a slower pulse rate. Heretofore, there was no method which enabled a person to determine how many heart pulses he had experienced over a predetermined length of time which would enable him to approximate the number of calories he had consumed or burned during that same length of time.

Therefore, it is the principal object of the invention to provide an electronic calorie counter.

A still further object of the invention is to provide a calorie counter which detects the heart pulses and which provides a visual display of the calories per minute and the calories which have been burned since a predetermined time.

A still further object of the invention is to provide a calorie counter which may be incorporated into a wristwatch configuration. A still further object of the invention is to provide a calorie counter which is economical of manufacture, durable in use and refined in appearance.

BRIEF DESCRIPTION OF THE DRAWINGS

FIG. 1 is a chart which compares the calorie burn rate versus the pulse rate:

FIG. 2 is a perspective view of the case configuration of the invention:

FIG. 3 is a block diagram of the circuitry of the invention; and

FIGS. 4–7 illustrate the electrical circuitry of the invention.

DESCRIPTION OF THE PREFERRED EMBODIMENT

Figure 5:
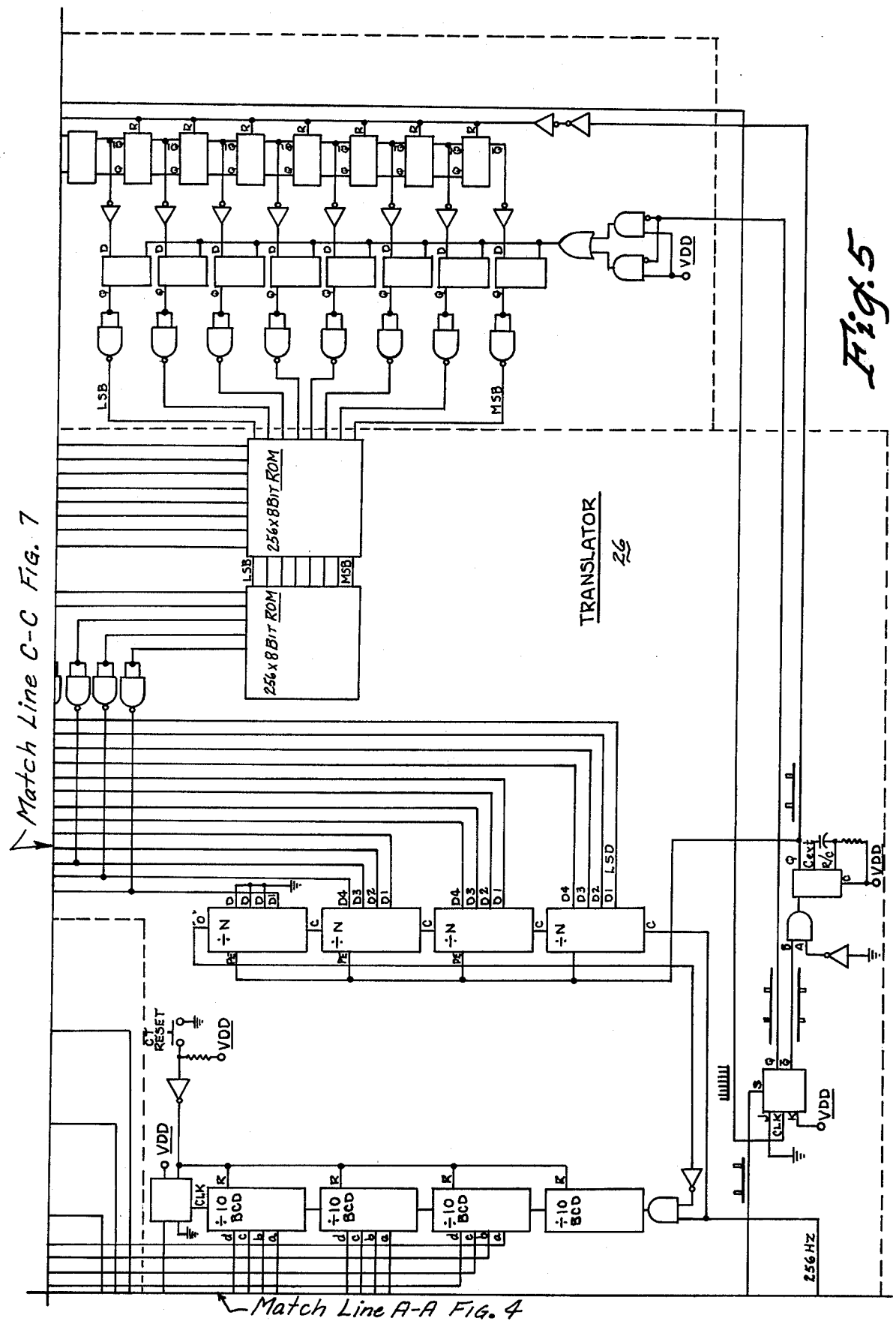
Figure 6:
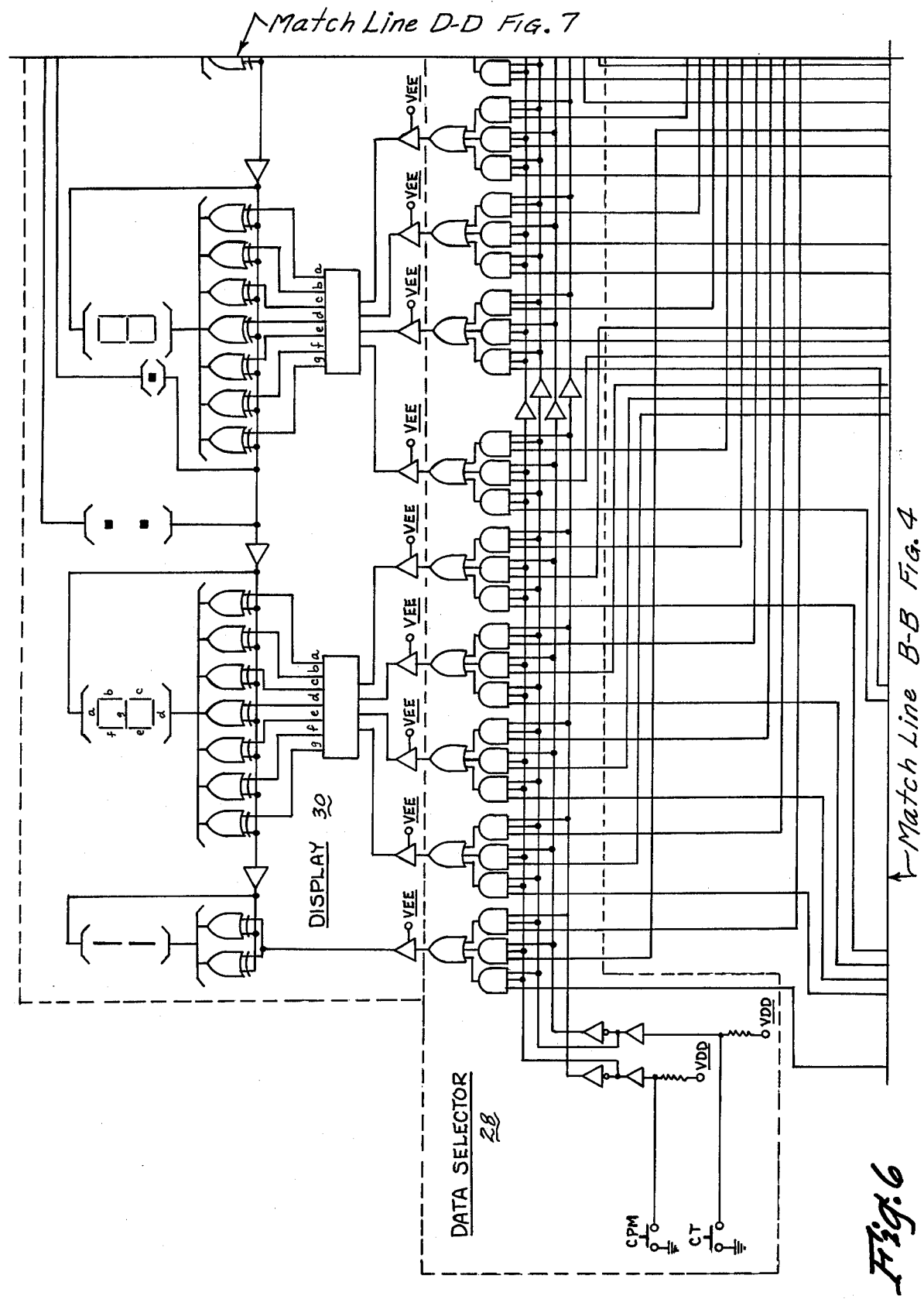
Figure 7:
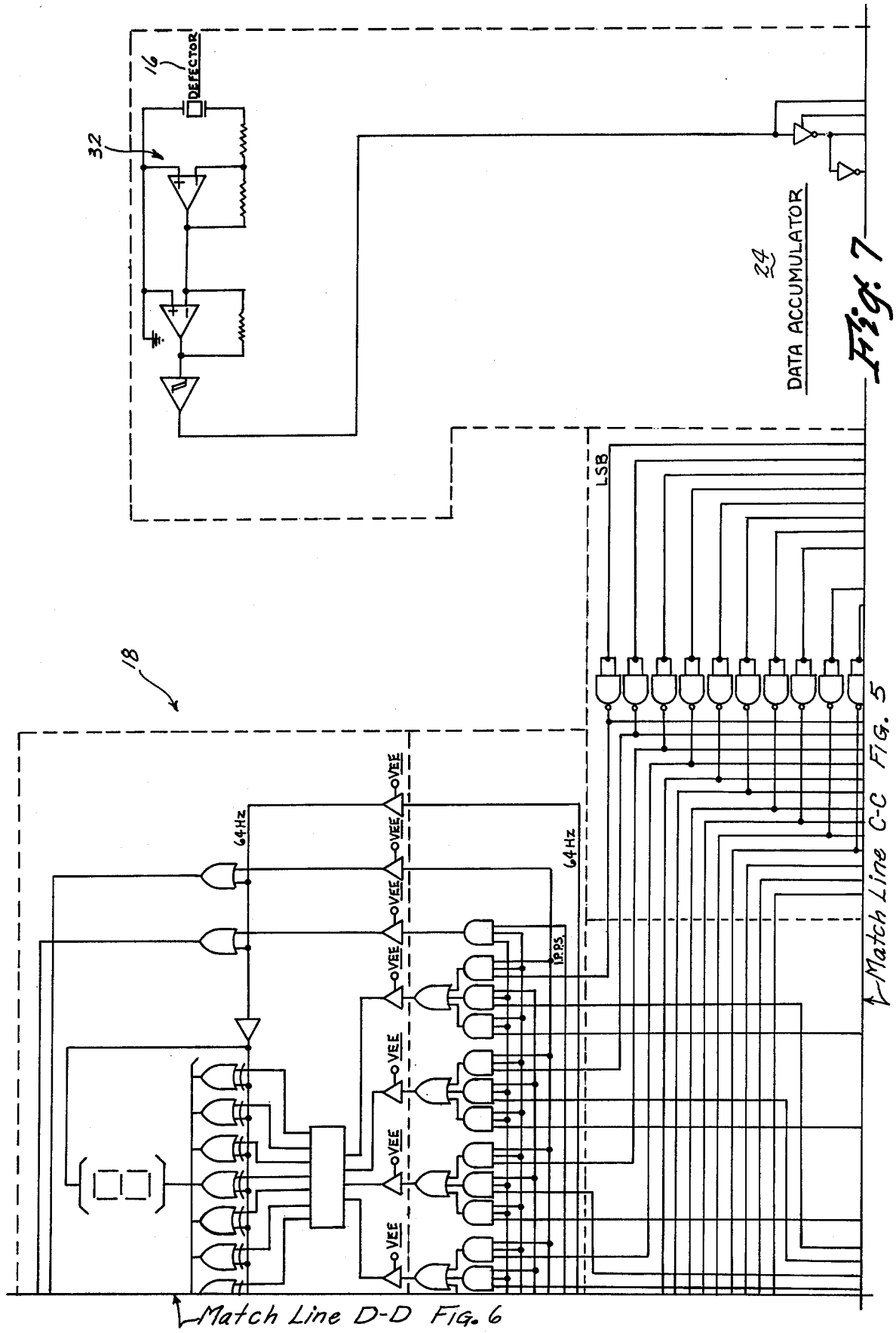

Referring to FIG. 2, the numeral 10 refers to a wristwatch type device including a display area 12 and a band 14. Band 14 is provided with a conventional pulse detector 16 mounted on the interior of the band 14 so as to detect the pulse of the wearer.

Referring to FIG. 3, it can be seen that the calorie counter circuit 18 is comprised of six sections: (1) time base section 20; (2) clock section 22; (3) data accumulator section 24; (4) translator section 26; (5) data selector section 28, and (6) display section 30. Data accumulator 24 generally includes amplifier 32, counter 34 and latch 36. Translator 26 generally includes a down counter 38, counter 40 and look-up memory 42. Time base section 20 is comprised of a 32.768 KHz crystal oscillator 42, trimming network 44 and frequency dividers generally referred to by the reference numeral 46. Display section 30 includes a driver circuit 48. The numeral 50 refers to a manual control to permit the selection of the desired format of display.

The time base section 20 provides the clock frequencies necessary to synchronize the operation of the circuits and counter sections. These frequencies as derived from the basic 32.768 KHz oscillator are: 256 pulses/second; 64 pulses/second; 1 pulse/second; and 1 pulse/minute. The clock section 22 utilizes the 1 pulse/minute for time keeping and the 1 pulse/second for updating and setting functions. The 1 pulse/minute is divided in the decade counters to provide a binary coded decimal output for the minutes, tens of minutes and hours. Decoder logic is used to provide a 12 hour format.

The heart pulses are detected by the pulse detector 16 and are amplified by the amplifier 32 and formed into uniform shaped waves and applied to the data accumulator section 24. The data accumulator section totalizes the pulse count for a time of one minute and thus determines the pulse rate. The pulse rate is held in the latch 36 and is updated at one minute intervals.

The pulse rate from the data accumulator latch 36 is applied to the look-up memory 42 of the translator 26 to obtain the correct calorie versus pulse rate relationship. The look-up memory 42 provides a direct calorie reading for each and every pulse rate from 40 pulses/minute to 199 pulses/minute. This calorie count is updated each minute with the input of pulse rate to the translator 26.

The calories count for each minute of time is preset into the divide by N down counters 38 and accumulated in the divide by ten binary coded decimal counters. This accumulation represents the total calorie count for a period determined by the calorie total manual reset.

The binary coded decimal output information from the clock 22 and the translator 26 are applied to the data selector 28 for synchronizing. The manual control 50 is used to select the desired format of display; i.e., time, calorie/minute, or calories total. It should be noted that time is the steady state format and other operations are obtained only by operation of the manual selection button 50.

One of the three available formats is applied to the driver circuit 48 which converts and processes the binary coded decimal information into drive lines for the display numbers. The display section also provides the necessary logic for the colon between the hours and minutes in the time format and a decimal point in the calorie/minute format.

Thus, a person upon arising in the morning could place the calorie counter 10 on his wrist and press the calorie total manual reset. At any time during the day, the wearer simply needs to operate the manual selection button 50 to determine his present calorie burn rate per minute or to determine how many calories he has burned since he placed the watch on his wrist. Thus, if a person determined that he had not burned very many calories during the day, he may want to engage in strenuous activity before retiring so that he would burn additional calories.

Thus it can be seen that a novel electronic calorie counter has been provided which accomplishes at least all of its stated objectives.

We claim:
1. An electronic calorie counter comprising,
a portable pulse detector means adapted to be attached to a person's wrist and worn during daily activities for detecting the heart pulse of the person,
electronic circuit means including an electronic counter means operatively connected to said pulse detector means for totalizing the detected pulses for a predetermined time for determining the pulse rate, electronic computer means operatively connected to said counter means for converting the detected pulse rate into the approximate calorie burn rate in response to programmed information in the computer means, said electronic computer means including means for computing the calorie burn total, for a predetermined length of time, in response to the computed calorie burn rate, and visual display means operatively connected to said means for computing the calorie burn total for displaying the computed calorie burn total.

2. The calorie counter of claim 1 wherein said electronic computer means comprises a translator circuit portion including a look-up memory programmed with a calorie versus pulse rate relationship to provide a direct calorie reading for a range of pulse rates.

3. The calorie counter of claim 1 wherein the pulse detector means and electronic circuit means are mounted within a housing strapped to the person's wrist, said pulse detector means and electronic circuit means being battery powered.

4. An electronic calorie counter comprising, a time base comprising an oscillator means, trimming network and frequency dividers to provide clock frequencies for synchronizing circuit operation and counter sections, said oscillator means providing frequencies of 256 pulses per second; 64 pulses per second; 1 pulse per second; and 1 pulse per minute, a clock connected to said time base for receiving the one pulse per second and one pulse per minute frequencies, a data accumulator means comprising a pulse detector, amplifier, counter means and latch means; said pulse detector detecting the heart pulses of the subject; said amplifier being electronically connected to said pulse detector for amplifying the heart pulses, means for forming the amplified heart pulses into uniformly shaped waves, said counter means being connected to said time base and said means for forming the amplified heart pulses into uniformly shaped waves for totalizing the pulse count for a predetermined time to determine the pulse rate, said latch means being connected to said counter means and said time base for holding a constantly updated pulse rate, a translator means comprising a look-up memory circuit connected to said latch means, a second counter means connected to said time base for receiving the 256 pulses per second frequency, a down counter means connected to said time base for receiving the 256 pulses per second frequency, said second counter means and said down counter means being electronically connected, said look-up memory circuit electronically connected to said down counter means, said look-up memory circuit being programmed with a range of calorie versus pulse rate relationships, said look-up memory circuit providing a constantly updated direct calorie count reading for a range of low to high pulse rates, a data selector means electronically connected to said clock and said translator means, said data selector means receiving binary coded output information from said clock and translator means which at least includes the computed calorie total as related to sensed heart pulses for a predetermined length of time, a manual control connected to said data selector for selecting the desired format of display, and a display circuit menas including a driver circuit which is electronically connected to said data selector and said time base, said driver circuit receiving the 64 pulse per second frequency from said time base, said driver circuit converting and processing the binary coded output information into drive lines for displayed numbers, said displayed numbers at least selectively displaying the computed calorie total which has been burned by the subject for a predetermined length of time corresponding to the heart pulses of the subject during said predetermined length of time.

5. The calorie counter of claim 4 wherein said displayed numbers normally display the time of day said manual control permitting the selection of the desired format of display other than the time of day.

6. The calorie counter of claim 1 wherein said displayed numbers selectively display the calories per minute presently being burned by the subject.

7. The calorie counter of claim 1 wherein said translator means includes a calorie total manual reset.

* * * * *